United States Patent [19]

Greenspan

[11] 4,409,988

[45] * Oct. 18, 1983

[54] APPARATUS FOR COLLECTING CULTURES

[75] Inventor: Donald J. Greenspan, 235 Pavilion Ave., Riverside, N.J. 08075

[73] Assignee: Donald J. Greenspan, Riverside, N.J.

[ * ] Notice: The portion of the term of this patent subsequent to Jan. 22, 1997 has been disclaimed.

[21] Appl. No.: 80,551

[22] Filed: Oct. 1, 1979

Related U.S. Application Data

[60] Division of Ser. No. 781,298, Mar. 25, 1977, Pat. No. 4,184,483, which is a continuation-in-part of Ser. No. 589,521, Jun. 23, 1975, Pat. No. 4,014,746, which is a continuation-in-part of Ser. No. 358,350, May 8, 1973, Pat. No. 3,890,954.

[51] Int. Cl.³ .............................................. A61B 10/00
[52] U.S. Cl. ..................................... 128/759; 435/294; 435/295
[58] Field of Search ................ 128/759, 269; 435/294, 435/295; 215/3; 206/210, 569, 363, 438, 15.2, 15.3, 606, 613, 623, 828

[56] References Cited

U.S. PATENT DOCUMENTS

| | | | |
|---|---|---|---|
| 3,163,160 | 12/1964 | Cohen | 128/759 X |
| 3,388,043 | 6/1968 | Ingvorsen | 128/759 X |
| 3,450,129 | 6/1969 | Avery et al. | 128/759 |
| 3,508,653 | 4/1970 | Coleman | 128/764 X |
| 3,579,303 | 5/1971 | Pickering | 128/269 X |
| 3,776,220 | 12/1973 | Monaghan | 128/759 |
| 3,890,204 | 6/1975 | Avery | 128/759 X |
| 3,913,564 | 10/1975 | Freshley | 128/759 |
| 3,918,435 | 11/1975 | Beall et al. | 128/269 X |
| 4,014,748 | 3/1977 | Spinner et al. | 128/759 X |

FOREIGN PATENT DOCUMENTS

| | | | |
|---|---|---|---|
| 285835 | 7/1915 | Fed. Rep. of Germany | 128/269 |
| 2248012 | 5/1975 | France | 128/759 |

*Primary Examiner*—George F. Lesmes
*Assistant Examiner*—Nancy A. B. Swisher
*Attorney, Agent, or Firm*—Woodcock, Washburn, Kurtz, Mackiewicz & Norris

[57] ABSTRACT

A swab is packaged in a tube having an open end and containing a culture-sustaining or bacteria identification liquid at the bottom of a tube, and a plug including a one-way isolating valve located above the liquid and a barrier member forming a leak-proof chamber between the plug and the barrier member. After removal of the swab from the tube and swabbing of a body canal or the like with the absorbent tip of the swab, the swab may be placed back in the tube with the absorbent tip adjacent the plug and within the substantially air-tight chamber. The plug may then be forced downwardly through the liquid by pressing on the end of the swab or another rigid member telescoped within the tube so as to force the liquid up through the valve into contact with the absorbent tip. A closure or cap which may be used to press on the end of the stick or the rigid member then forms a seal at the open end of the tube.

3 Claims, 34 Drawing Figures

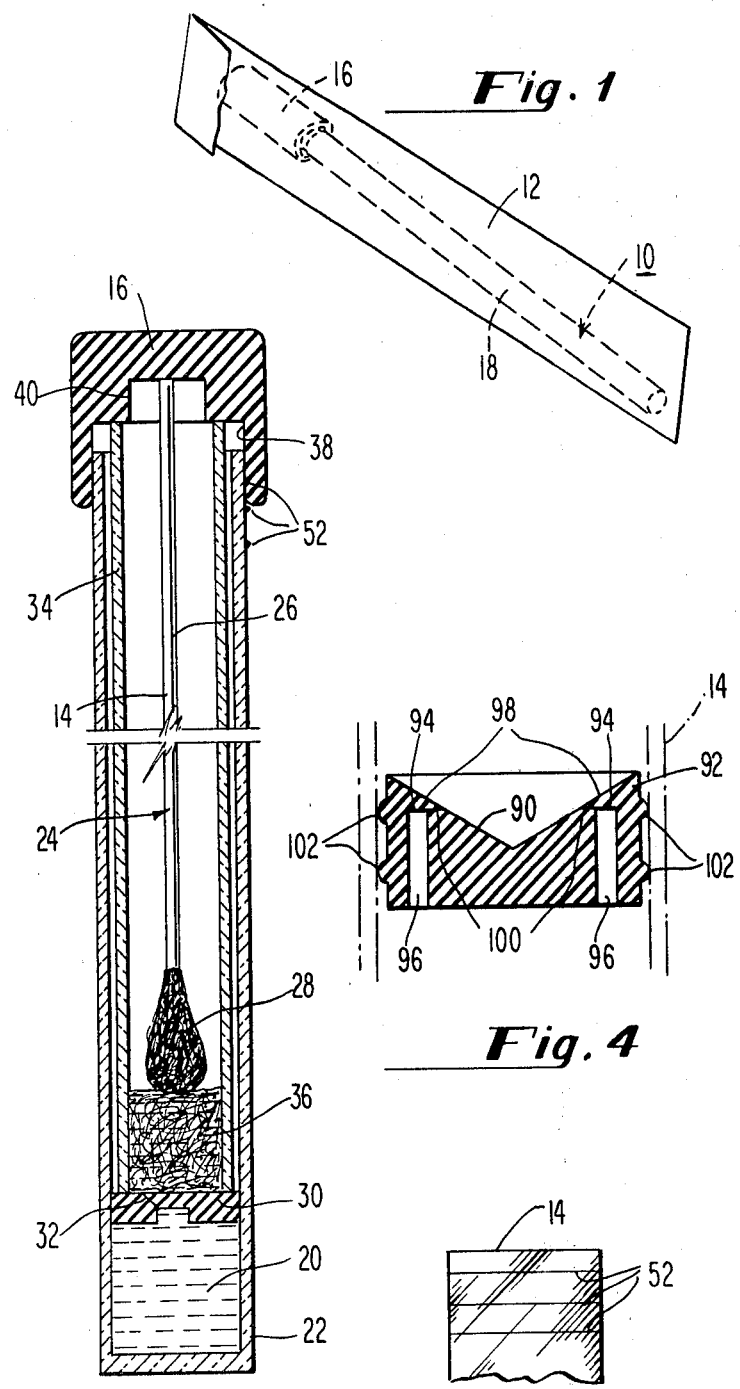
Fig. 1
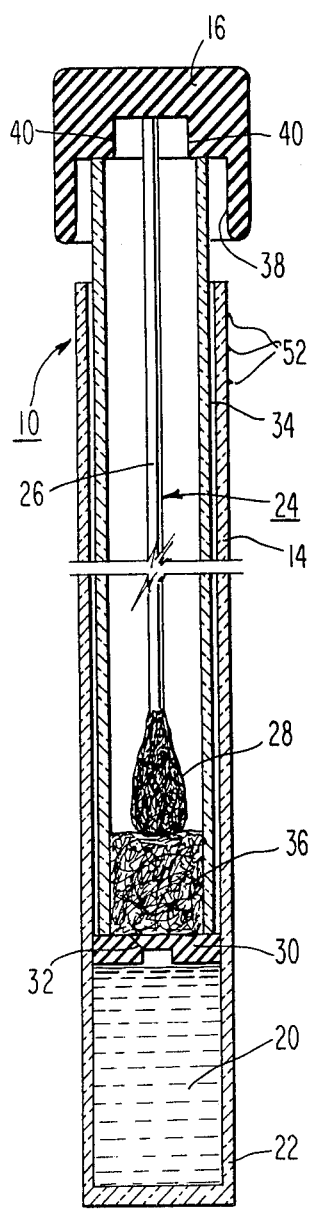
Fig. 2
Fig. 3
Fig. 2b
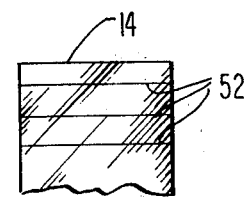
Fig. 4
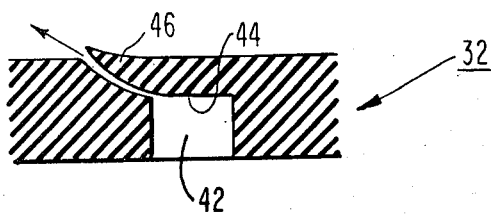
Fig. 2a

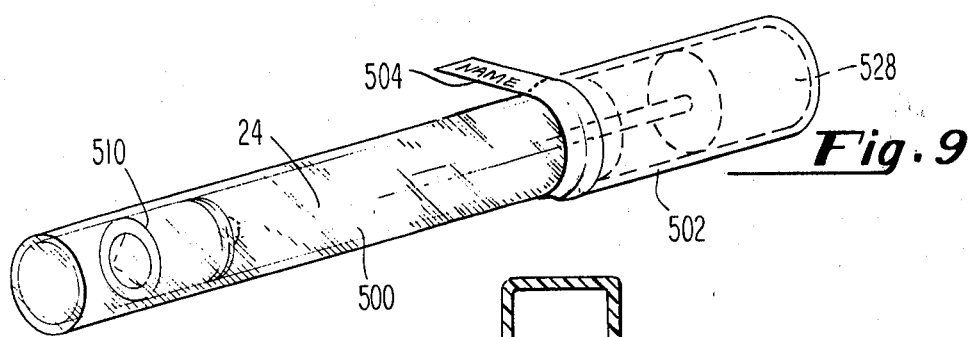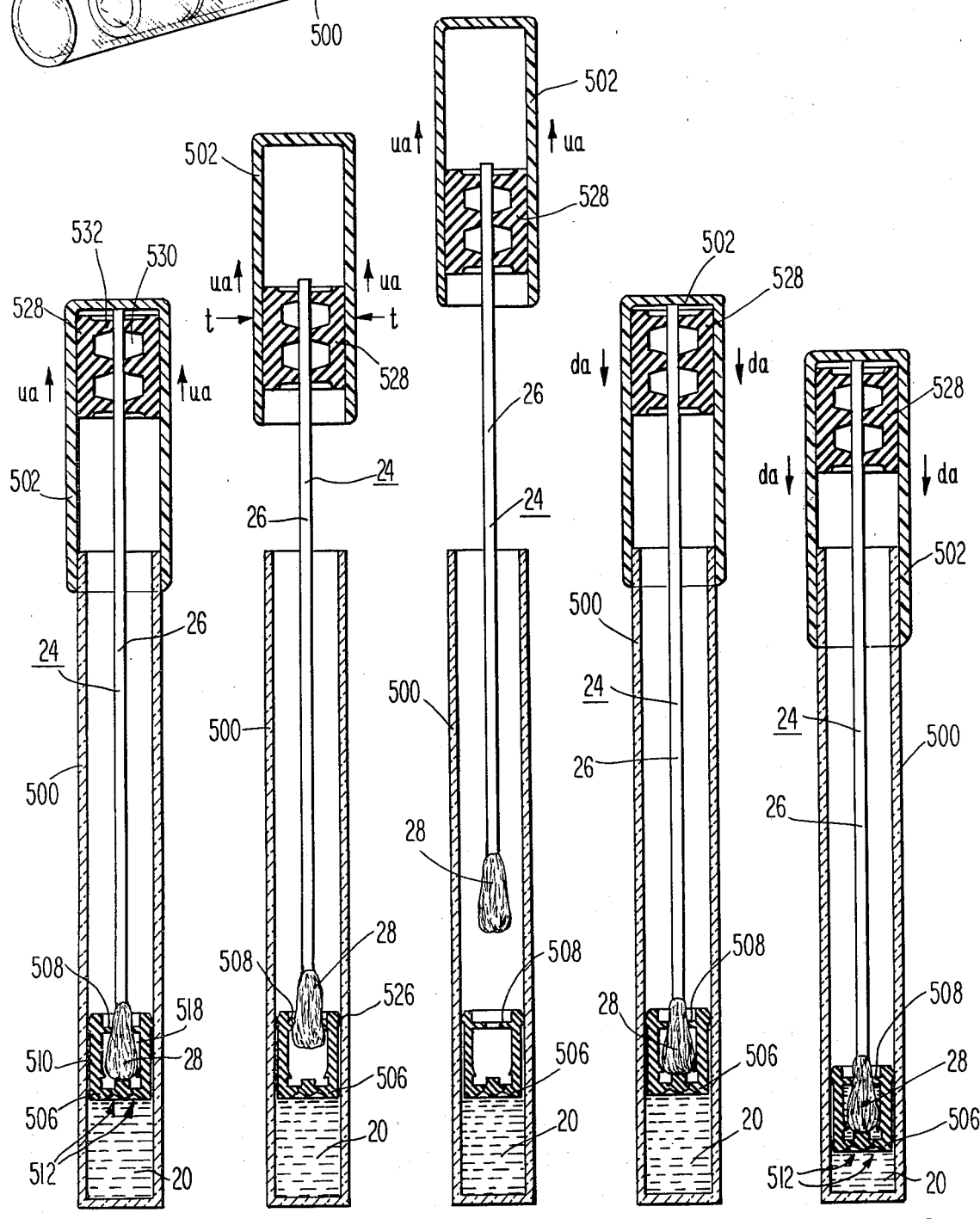
Fig.9  Fig.10  Fig.11  Fig.12  Fig.13  Fig.14

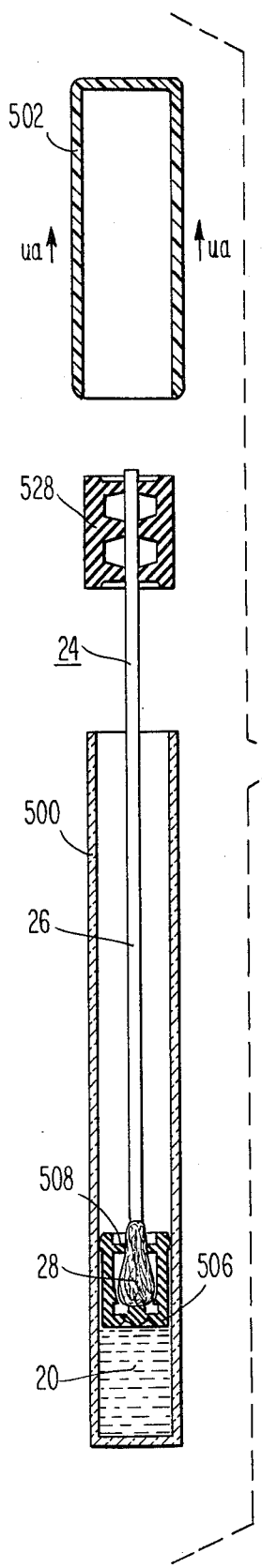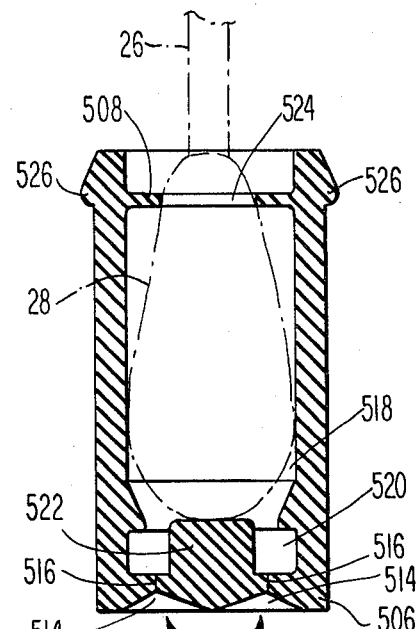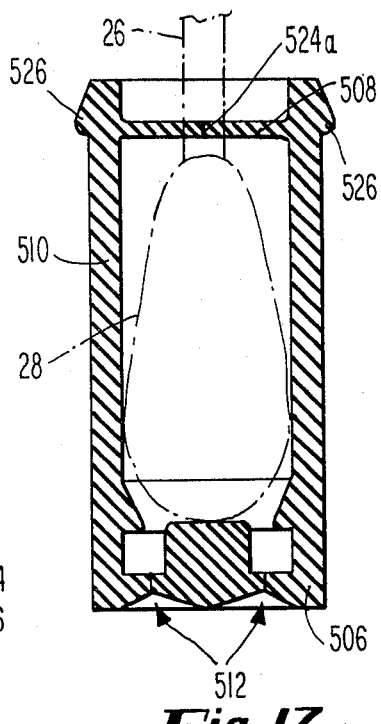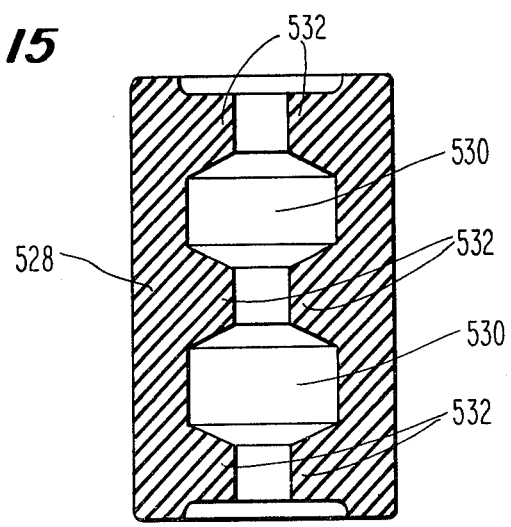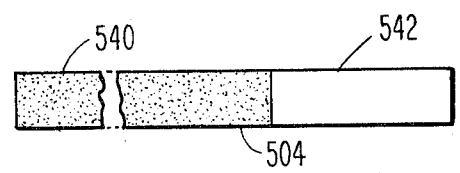

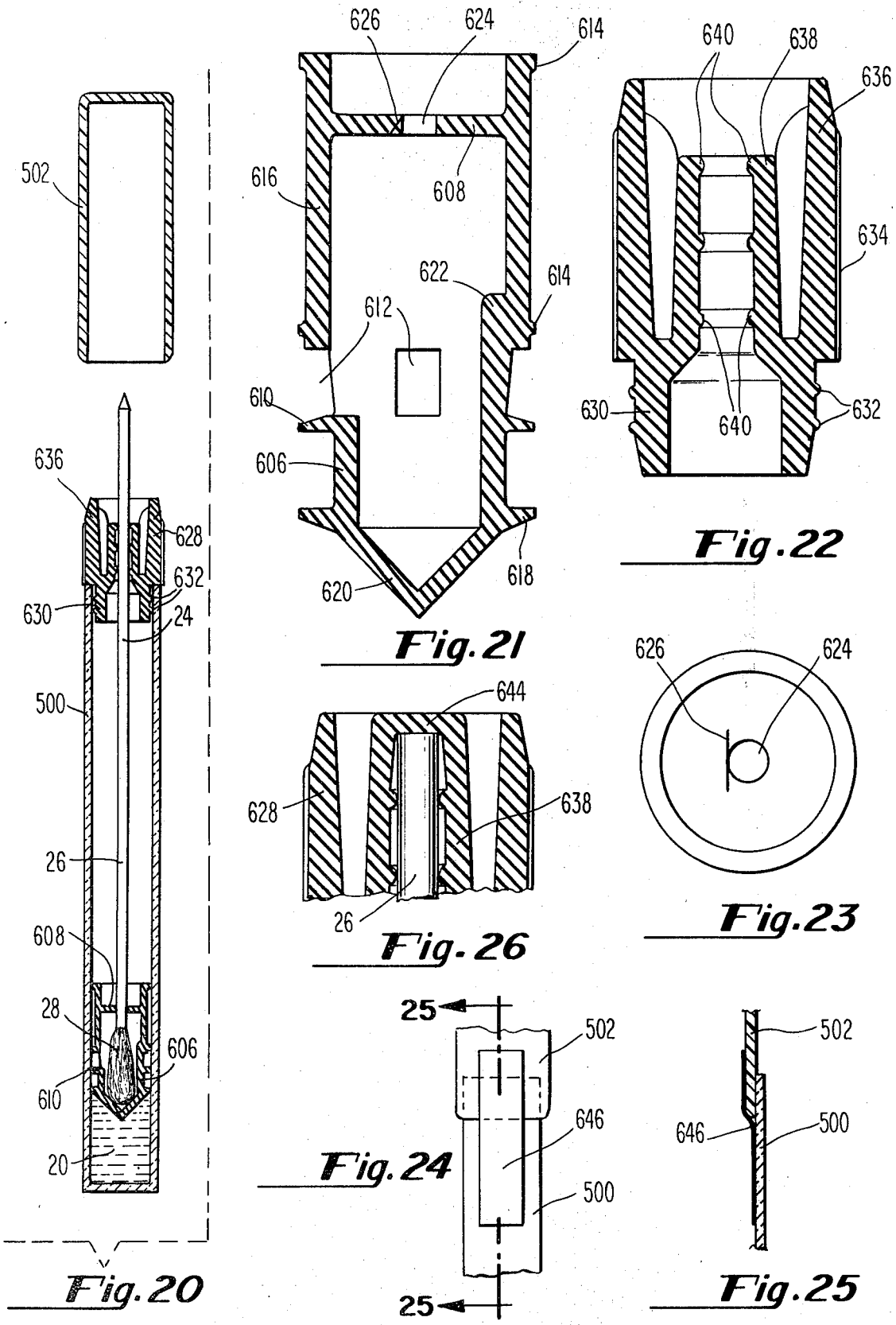

APPARATUS FOR COLLECTING CULTURES

RELATED CASES

This is a division of application Ser. No. 781,298 filed Mar. 25, 1977, U.S. Pat. No. 4,184,483, which is a continuation-in-part of application Ser. No. 589,521, filed June 23, 1975, U.S. Pat. No. 4,014,746, which is a continuation-in-part of Ser. No. 358,350, filed May 8, 1973, U.S. Pat. No. 3,890,954.

BACKGROUND OF THE INVENTION

This invention relates to a swabbing method and apparatus for use by physicians and technicians for collecting a culture as from various areas of a patient's body, such as the ears, the nose and throat, and for keeping a culture moist and alive for a period of time after it is collected or for use in identifying the bacteria of the culture.

In general, this is accomplished through the use of a container which receives the culture-carrying swab and bathes the swab in a culture-sustaining liquid. U.S. Pat. No. 3,450,129—Avery et al discloses a particular container unit for this purpose. The container carries its own supply of liquid in a frangible ampoule along with a swab, all of which is packaged in a sanitary wrapper. After the swab has been removed from the wrapper and container and a culture has been taken, the swab is inserted back into the container, a cap is applied to the end of the container and the frangible ampoule is broken so as to bathe the absorbent tip of the swab in the culture-sustaining liquid which was encapsulated in the ampoule.

Another container is disclosed in the U.S. Pat. No. 3,776,220—Monaghan. The container also carries its own sealed supply of liquid below a first sealed area in the tube and the swab itself, prior to use, is located in the tube such that the absorbent tip is positioned immediately above the sealed area and below a restricted area. After the culture is taken, the swab is reinserted into the container, through the restricted area and the sealed area so as to reach the culture-sustaining liquid at the bottom of the tube. The sealed area immediately above the culture-sustaining liquid no longer forms a seal but permits air to enter the area of the absorbent tip and the culture-sustaining liquid.

Another container is disclosed in the U.S. Pat. No. 3,163,160-Cohen which utilizes a member including a valve initially positioned above the culture-sustaining liquid. After the culture has been taken, the bottom of the container may be squeezed so as to force the culture-sustaining liquid upwardly through the valve into saturating contact with the absorbent tip of the swab. There is no movement of the valve member in response to movement of the swab or the absorbent tip. In fact, the absorbent tip of the swab does not contact the valve member.

U.S. Pat. No. 3,579,303-Pickering discloses a flexible swab container in combination with a clip which may be utilized to form a seal between the flexible container and the elongated member which extends to the absorbent tip of the swab which is submersed in a culture-sustaining liquid. Still another sampling unit is disclosed in U.S. Pat. No. 3,388,043-Ingvorsen.

German Pat. No. 285,835 discloses a container including a valve member for use in moistening a swab with a disinfecting liquid. However, the swab itself is not used to force the plug through the disinfecting liquid. Rather, a plunger connected to the plug from the other side of the swab moves the plug through a tube.

U.S. Pat. No. 3,508,653-Coleman discloses a plug having a valve for serum separation. It does not however suggest that such a valve could be utilized in combination with a swab stick to control the introduction of a culture-sustaining liquid into contact with the absorbent tip of the swab.

SUMMARY OF THE INVENTION

It is a general object of this invention to provide new and improved apparatus for collecting cultures.

In accordance with one important aspect of the invention, the apparatus comprises a movable piston member extending across the tubular container and in sealing engagement with both sides thereof between the closed end and the barrier member. The piston member is movable through the culture-sustaining liquid toward the closed end when the swab is in pushing contact with the piston member. The piston member includes a valve means for allowing the culture-sustaining liquid to pass from a chamber formed between the closed end and the piston member and enter the chamber within the piston member when the swab is in pushing contact with the piston member.

In one preferred embodiment of the invention, the valve means comprises a flange which forms a seal with the hollow tubular container while also allowing the culture medium to pass into the chamber.

In accordance with another important aspect of the invention, the absorbent tip of the swab may be inserted into and withdrawn from the chamber without substantially moving the piston member or the barrier member.

BRIEF DESCRIPTION OF THE DRAWINGS

FIG. 1 is a perspective view of a culture collecting apparatus embodying the invention in its wrapper;

FIG. 2 is a sectional view of the culture collecting apparatus embodying the invention;

FIG. 2a is an enlarged view of a valve in the plug of the culture collecting apparatus shown in FIG. 2;

FIG. 2b is a partial elevational view of the markings on the container tube shown in FIG. 2;

FIG. 3 is a sectional view of the apparatus of FIG. 2 after the culture-carrying swab has been sealed into its container tube;

FIG. 4 is a sectional view of a piston member or plug which may be utilized in the apparatus of FIGS. 2 and 3;

FIG. 9 is a perspective view of a culture collecting apparatus which represents another embodiment of this invention;

FIG. 10 is a sectional view of the embodiment shown in FIG. 9 during opening;

FIG. 11 is a sectional view of the embodiment shown in FIG. 9 at a subsequent time during opening;

FIG. 12 is a sectional view of the embodiment shown in FIG. 9 during the last stage of opening;

FIG. 13 is a sectional view of the apparatus shown in FIG. 9 after use of the swab and during insertion of the swab back into the container;

FIG. 14 is a sectional view of the apparatus shown in FIG. 9 after use and during saturation of the absorbent tip of the swab in the culture-sustaining medium;

FIG. 15 is a sectional view of the apparatus of FIG. 9 showing another mode of use of the apparatus;

FIG. 16 is an enlarged sectional view of the chamber shown in the apparatus of FIGS. 10–15 which receives the absorbent tip of the swab;

FIG. 17 is an enlarged sectional view of a chamber in an anaerobic apparatus representing another embodiment of the invention;

FIG. 18 is an enlarged sectional view of the terminal bulbous portion of the swab which is received by the cap in the apparatus shown in FIGS. 10–15;

FIG. 19 is a flexible tape-like member which forms the seal between the container and the cap shown in FIG. 9;

FIG. 20 is a sectional view of a culture collecting apparatus representing a still further embodiment of the invention;

FIG. 21 is an enlarged view of the portion of the collection apparatus of FIG. 20 which forms the chamber receiving the absorbent tip;

FIG. 22 is an enlarged sectional view of the bulbous portion of the swab shown in FIG. 20;

FIG. 23 is an end view of the member shown in FIG. 21;

FIG. 24 is an elevational view of the apparatus of FIG. 20 showing an adhesive label-like member joining the cap and the hollow container;

FIG. 25 is a sectional view taken along lines 25—25 of FIG. 24;

FIG. 26 is a sectional view of the modified bulbous portion shown in FIG. 22;

DETAILED DESCRIPTION OF PREFERRED EMBODIMENTS

Figure 5:
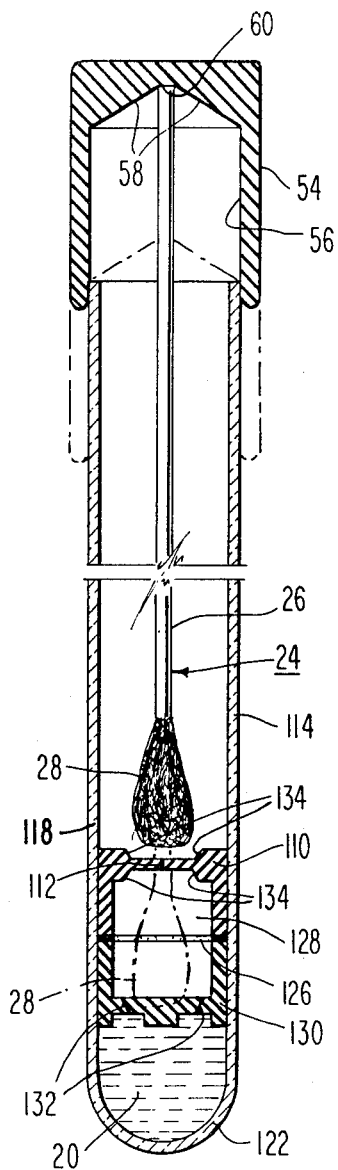
FIG. 5 is a sectional view of a culture collecting apparatus representing another embodiment of the invention.

A swabbing apparatus 10 constructed in accordance with this invention for use in obtaining cultures is enclosed within a wrapper 12 comprising paper or the like as shown in FIG. 1. As shown in FIG. 2, the apparatus 10, which has been removed from the wrapper 12 of FIG. 1, comprises a container tube 14 and a closure member or cap 16 which is not sealed to the upper and open end 18 of the tube 14. The tube 14 contains a culture-sustaining liquid 20 within a chamber formed at the closed end or bottom 22 of the tube 14 and remains isolated from a swab 24 comprising an elongated member or stick 26 and an absorbent tip 28. This isolation is achieved by a piston-like plug 30 comprising a substantially resilient material such as rubber or plastic so as to resiliently and sealingly engage the walls of the tube 14.

The plug 30 includes a one-way valve 32 which allows the liquid 20 to flow through an opening in the plug 30 when the plug is forced downwardly into the liquid 20 but maintains substantial physical isolation between the absorbent tip 28 of the swab 24 and a culture-sustaining liquid when the plug 30 is in the position shown in FIG. 2.

The tube 14 also contains an inner tube 34 on which the cap 16 (the cap is shown as shortened in length because of space limitations of the drawings) is resting which forms a chamber spaced and isolated from the sides of the tube and within which the swab 24 is located. An absorbent material 36 such as cotton, rayon or a foam is located within the chamber formed by tube 34 supporting the tip 28 above the plug 30.

Once the apparatus 10 has been removed from the wrapper 12 as shown in FIG. 2, the cap 16 may be removed from the upper end of the inner tube 34. A swab 24 may then be grasped between the finer tips at the upper end protruding from the inner tube 34 and removed from the tube 14. At that time, the absorbent tip 28 may be brought into contact with that portion of the body from which a culture is to be taken and reinserted back into the inner tube 34.

At this time, the plug 30 is pushed downwards through the liquid 20 by pressing on the cap 16 which in turn presses on the upper end of the inner tube 34 so as to transmit the downward force therethrough to the plug 30 moving it to the position shown in FIG. 3. Note that the level of the liquid 20 now extends above the bottom of the inner tube 34 so as to saturate the absorbent material 36 and thereby assure that the tip 28 remains moist to keep the culture alive.

In order for the cap 16 to perform this pushing function with respect to the plug 30, the inside of the cap has a particular configuration. An elongated sealing surface 38 is provided which is adapted to engage the outside of the container tube 14 so as to isolate, at least to some degree, the contents of the tube once the surface 38 has been brought into contact with the outside of the tube 14. In addition, the cap 16 includes a shoulder which extends substantially perpendicular to the axis of the cap 16 so as to provide a surface which pushes against the upper end of the tube 34. Finally, the cap 16 includes a recess 40 which receives the upper end of the swab stick 26. The recess 40 has slightly less depth than the protrusion of the swab stick 26 beyond the end of the tube 34 to assure the swab 24 is, to some degree, forced into the cotton 36.

The nature of the one-way isolating valve in the plug 30 is shown in some detail in the enlarged view of FIG. 2a. The valve 32 includes a hole 42 which extends upwardly from the underside of the plug 30. An inclined slit is provided which extends from the upper surface of the plug 30 at one side of the hole 42 down to the upper end of the hole 42 so as to form a flap 46 which is biased to the closed position when the plug 30 is stationary within the liquid 20 and pressure on the opposite side of the plug 30 are substantially equal. It will be understood that the bias to maintain the resilient flap 46 closed even when there is some pressure differential between opposite sides of the plug to be sure that the valve remains closed even when the tube 14 is inverted. For other details relating to the nature of this valve, reference is made to the inventor's own U.S. Pat. No. 3,661,265.

In accordance with another important aspect of the invention, a culture-sustaining liquid may be periodically introduced into the area above the plug 30 so as to extend the period in which the culture may be kept alive. For this purpose marks 52 shown in FIGS. 2 and 2b are provided on the exterior and upper end of the tube 14. When the cap is first placed on the tube 14 after the culture has been taken, it is pushed down to the first of the marks 52. It may then be sequentially advanced to the other marks at desirable intervals, e.g., every 24 hours, to keep reintroducing the liquid into contact with the absorbent material 36 and the absorbent tip 28 of the swab 24.

FIG. 4 discloses another plug or piston member 92 which may be substituted for the plug 30 of FIGS. 2 and 3. The plug 92 includes a downwardly and inwardly tapering surface 90 which, when utilized in conjunction with a similarly tapered cap which will be described with reference to FIG. 5, will serve to center the freely movable swab 24 along the axis of the tube thereby assuring the central, axially directed force on the plug 92. In addition to centering the tip 28 of the swab 24 on the plug 92, the tapered surface 90 also allows the swab 24 to assist in opening spaced one-way valve 94 which are located near the periphery of the plug 92. The valves 94 include elongated holes 96 extending substantially parallel with the axis of the plug and terminated by flaps 98 which are formed in part by the tapered surface 90. By observation it will be seen that any pressure located in the central area of the surface 90 will tend to collapse areas 100 of the plug beneath the flaps 98 so as to assist in opening the valves 94. It will also be seen that at least one valve 94 will be clear of the tip 28 to permit it to open.

Another embodiment of the invention is shown in FIG. 5 wherein a barrier member 110 extends across the tube 114 so as to form a substantially leak-proof barrier between a closed end or bottom 122 of the tube 114 and an open end so as to form a chamber 128 for the tip 28 of the swab 24. A plug member 130 includes a pair of valves 132 similar to the valves 32 as shown in FIG. 2a. The barrier member 110 and the plug 130 may be attached to one another by a suitable adhesive 126 or other means of affixing the barrier 110 in the plug 130.

After the absorbent tip 28 is inserted through the opening 112 and a seal is formed around the elongated member 26 of the swab 24, the swab 24 may be pushed downwardly so as to force the barrier member 110 and the plug member 130 downwardly through the culture-sustaining liquid 20 located at the bottom or closed end 122 of the tube. As the plug member 130 and the barrier member 110 advance toward the closed end 122, the culture-sustaining liquid moves upwardly through the valves 132 into the chamber 128. By moving the plug 130 sufficiently far through the culture-sustaining liquid 20, the chamber 128 may be substantially filled so as to eliminate or at least substantially eliminate all oxygen within the chamber 128.

The barrier member 110 comprises a suitable elastic material such as Kraton, supplied by Shell Chemical or TPR, supplied by Uniroyal, which will permit the opening 112 to enlarge thereby allowing the absorbent tip 28 of the swab 24 to pass therethrough while at the same time permitting the barrier member 110 to achieve sealing engagement with the elongated member 26 after the absorbent tip enters the chamber 128.

The barrier member 110 comprises a greater thickness near the sides of the tube 118 than near the opening 112. This sectional configuration of the barrier member 110 permits sufficient flexibility of the barrier member at the opening 112 to allow insertion of the absorbent tip 28 while at the same time permitting the barrier member 110 to snap back into a sealing position around the elongated member 26 of the swab 24. As shown in FIG. 5, it may also be desirable to provide tapering portions 134 which lead from the area of greater thickness to the area of lesser thickness adjacent the opening 112.

As shown in FIG. 5, chamber 128 becomes substantially air-tight after the absorbent tip 24 has been inserted therein. Accordingly, it is possible to utilize the culture-collecting apparatus of FIG. 5 for anaerobic cultures by the proper choice of the culture-sustaining liquid medium 20. An anaerobic liquid medium which has been found to be particularly appropriate is Stuart's Modified Media manufactured by Difco Laboratories.

In accordance with another important aspect of the embodiment shown in FIG. 5, a cap 54 is provided with a skirt including an internal sealing surface 56 engaging the outside walls of the tube 114 and a recess comprising upwardly and inwardly tapered walls 58 leading to a flat surface 60 near the top of the cap 54. The purpose of the taper 58 is to provide a surface which will center the upper end of the elongated member or stick 26 with respect to the cap 54 and thereby direct the forces applied to the cap substantially axially downwardly through the tube 14 to move the plug 130 through the liquid 20 as shown in FIG. 5. Without the taper 58, the elongated member 26 may be off-center with respect to the cap 54 and this would apply a nonaxial force to the plug 130 with the possibility of skewing it within the tube 114. Although this skewing would still permit the liquid to saturate the absorbent material of the tip 28, it would not permit the controlled periodic introduction of the liquid into contact with the tip 28 as is considered highly desirable.

Figure 6:
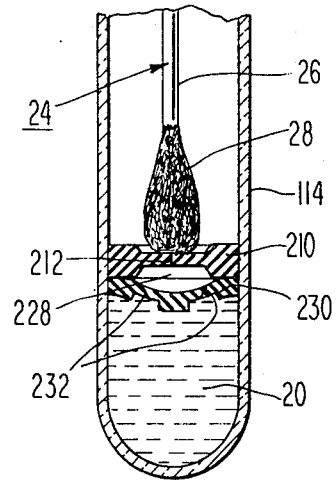
FIG. 6 is a sectional view of a culture collecting apparatus representing still another embodiment of the invention.
Figure 6A:
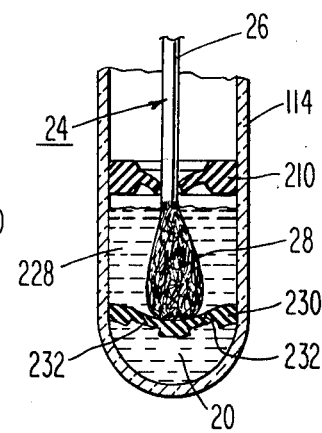
FIG. 6a is a sectional view of the apparatus of FIG. 6 after the swab has been inserted into the culture-sustaining or transport position.

Another embodiment of the invention is shown in FIG. 6 wherein a barrier member 210 is separable or detached from a plug or piston member 230. As shown in FIG. 6a, insertion of the absorbent tip through an opening 212 to a position which forces the plug member 230 downwardly and forms a chamber 228 which becomes filled with the culture-sustaining liquid 20 which passes through valve 232. The chamber 228 which is formed in part by the barrier member 210 as well as the plug 230 and the sides of the tube 114 is substantially air-tight so as to again permit the taking of anaerobic cultures assuming the use of the proper culture medium 20.

It will be noted that the piston member 230 in FIGS. 6 and 6a tapers inwardly and toward the closed end so as to direct the swab toward the central region of the piston member. In addition, the tapering provides a slightly performed chamber 228 which allows a substantial portion of the tip 28 to enter the chamber 228 before any culture-sustaining liquid passes through the valves 232 as the plug or piston 230 is advanced toward the closed end of the tube. This in turn minimizes the amount of culture-sustaining liquid which is permitted to pass through the opening 212 before the opening comes in sealing engagement with the elongated member 26 of the swab 24.

Figure 7:
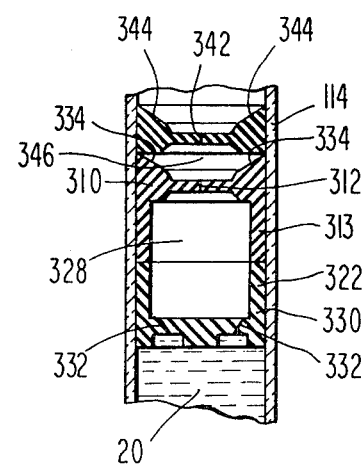
FIG. 7 is a sectional view of a culture collecting apparatus representing a further embodiment of the invention.

In the embodiment of FIG. 7, a barrier member 310 is utilized in combination with a separable piston or plug member 330 including axially extending walls 313 and 322 which provide a chamber 328 having an axial length capable of accommodating substantially all of the absorbent tip 28 of the swab 24 shown in FIGS. 5 and 6 before the contact is made between the tip 28 and the bottom of the plug 330. As in the embodiments of FIGS. 5 and 6, the plug portion 310 includes valves 332. In addition, the barrier member 310 includes tapered surfaces 334 which taper inwardly and downwardly so as to direct the tip 28 of the swab 24 toward the opening 312.

Another barrier member 340 is shown in FIG. 7 as comprising an opening 342. The barrier member 340 which includes a tapered surface 344 is adapted to form an isolating chamber 346 above the barrier member 310 so as to assure that the culture sustaining liquid is isolated from the open end of the container 114. Such an additional barrier member can be advantageously utilized in the embodiment of FIG. 6 to prevent the culture-sustaining liquid from squirting or traveling up the container 114 when the plug 230 is moved downwardly. Of course, as the swab 24 is forced downwardly, the plug 330 will separate from the barrier member 310 while culture-sustaining liquid is introduced through the valves 332. By providing the rather large chamber 328 before the plug member 330 is moved through the culture-sustaining liquid, a seal at the opening 312 may be formed around the elongated member 26 before the culture-sustaining liquid enters the chamber 328 so as to substantially preclude leakage of the culture-sustaining liquid upwardly beyond the barrier 310.

Figure 8:
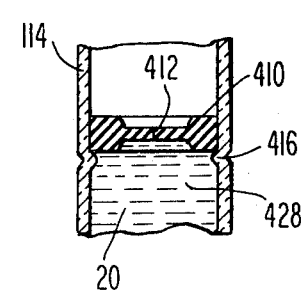
FIG. 8 is a sectional view of a culture collecting apparatus representing still a further embodiment of the invention.

The embodiment of FIG. 8 shows a barrier member 410 without any plug portion so as to form a chamber 428 between the barrier member 410 and the closed end of the tube 114. In order to hold the barrier member 410 in place, the tube 114 includes radially inwardly extending projections 416. The barrier member 410 includes an opening 412 which receives the absorbent tip 28 of the swab 24 and forms a seal around the elongated member 26 after passage of the absorbent tip 28 through the opening 412. As in the embodiment of FIGS. 5–7, the cross sectional thickness of the barrier member 410 at the opening 412 is less than the thickness of the barrier 410 adjacent the sides of the tubular member 214.

In the embodiments of FIGS. 5–8, it is particularly important that the seal formed around the openings 112, 212, 312 and 412 be substantially fluid tight. This assures that the culture-sustaining liquid will be retained within the chamber below the barrier member. In addition, it permits the use of the apparatus in collecting anaerobic cultures by assuring that air cannot enter the chamber within which the absorbent tip 28 is located.

It has been found particularly desirable to utilize an opening which is of a configuration of the elongated member 26. For example, if the elongated member 26 has a cross sectional configuration which is circular, the openings 112, 212, 312 and 412 should be substantially circular. On the other hand, if the cross sectional configuration of the elongated member 26 is rectangular, the openings should be rectangular.

In another embodiment shown in FIG. 9, the need for a wrapper such as that shown in FIG. 1 is eliminated. More particularly, a hollow tubular container or tube 500 is covered by a hollow tubular cap 502 which receives the end of the tube 500 and both the tube 500 and the cap 502 are adhesively sealed by a flexible, elongated tape-like member 504. Since the swab 24 and related apparatus which will be described in detail are sterilely housed within the tube 500 and the cap 502 through the use of the tape-like member 504, there is no need for a wrapper.

The swab 24 and the related apparatus shown in FIG. 9 will now be described in detail with reference to FIG. 10, FIG. 16 and FIG. 18. As in the previous embodiments, the absorbent tip 28 is capable of being substantially housed within a leak-proof chamber. The leak-proof chamber is formed between a piston member 506 and a barrier member 508 which are joined by integral walls 510.

As best shown in FIG. 16, the piston member 506 comprises a plurality of off-center valves 512 which are adapted to permit the flow of the culture-sustaining liquid 20 through the valves 512 as the piston member 506 as well as the barrier member 508 are advanced downwardly through the culture-sustaining liquid 20. Valves 512 are formed by tapered openings 514 which terminate in slits 516 which extend parallel to the axis of the container 500 and communicate with the chamber 518. In order to prevent the tip 28 of the swab 26 from interfering with the valves 512, the slits 516 are recessed with respect to the tip 28. This recess is achieved by an annular depression 520 which surrounds a central abutment 522 upon which the tip 28 rests.

The barrier member 508 includes an opening 524 having a maximum cross-sectional dimension or diameter which is substantially larger than the diameter of the elongated member or stick 26 of the swab 24. This permits a portion of the tip 28 to extend through the opening 524 so as to enable the tip 528 to breathe through the opening. This breathing through the opening 524 permits the use of the apparatus in an aerobic application. At the same time, an adequate seal is formed between the barrier member 508 and the tip 28 at the opening 524 so as to assure that the chamber 518 is substantially leak-proof, i.e., the gravity flow of any culture-sustaining medium from the chamber 518 out through the opening 524 is substantially prevented. Note that the spacing between the barrier member 508 and the piston member 506 at the central abutment 522 is less than the overall axial length of the tip 28 so as to assure that a portion of the tip will extend through the opening 524.

The chamber as shown in FIGS. 10 and 16 also differs from that shown in previous embodiments in that a single seal is formed with the tube or container 500. This seal which is achieved by a modest flange 526 is located adjacent the barrier member 508. It will of course be appreciated that additional sealing surfaces may be established along the chamber 518 although this single sealing surface has been found to be adequate.

As shown in FIGS. 10 and 18, the end of the swab 24 spaced from the tip 28 comprises a bulbous portion 528. The bulbous portion 528 is formed by an elastic member having a central opening 530 which is adapted to receive the stick 26. The opening 530 is formed in part by a series of flanges 532 which slideably grip the stick 26. In the preferred embodiment, the bulbous portion or member 528 comprises the same elastic material as the piston member 506 and the barrier member 508, preferably Kraton.

In a preferred embodiment of the invention, the bulbous member 528 grips the stick 26 sufficiently hard so as to permit the member 528 to support the swab 24 without any pressure being applied transversely to the axis of the swab 24. At the same time, the bulbous member 528 is sufficiently large so as to form a modest friction fit with the cap 502 thereby permitting the cap 502 to support the swab 24 and the bulbous member 528 without any force transverse to the axis of the swab 24. However, as will now be described in detail, the friction fit between the bulbous member 528 and the cap 502 is not sufficient to pull the tip 28 out of the chamber 518, i.e., the friction fit between the tip 28 and the barrier member 50 at the opening 524 exceeds the friction fit between the cap 502 and the bulbous member 528. Accordingly, it becomes necessary to apply a transverse pressure to the cap 502 adjacent the bulbous member 528 if one desires to pull the tip 28 from the chamber 518.

As shown in FIG. 10, the cap 502 is subjected to an upward axial force depicted by arrows ua so as to begin to pull the tip 28 from the chamber formed between the barrier member 508 and the piston member 506. In the absence of a transverse force being applied to the cap 502, the bulbous member 528 slides freely along the cap 502 to the position shown in FIG. 11 while the tip 28 remains within the chamber as shown in FIG. 10.

In FIG. 11, a transverse force as depicted by t is combined with the upward axial force ua so as to pull the tip 28 through the opening in the barrier member 508. Note that the seal formed at the flange 526 is adequate so as to retain the barrier member 508 and the piston member 506 in place while the tip 28 is removed from the chamber.

As shown in FIG. 12, the entire swab 26 plus the bulbous member 528 is moved upwardly by the application of a mere upward axial force ua without any transverse force. It will further be noted that the effective length of the swab 24 is extended by the cap 502 which is important in many applications where a longer swab is desired. Once completely removed from the container 500, the swab 24 as extended by the cap 502 may be utilized to swab an area of culturable materials.

In FIG. 13, the swab 24 carried by the cap 502 has been reinserted into the container 500. Note that the bulbous member 528 is driven upwardly so as to seat on the top of the cap 502. Once seated, further downward movement of the cap 502 meters in predetermined amounts of the liquid 20 through the valves 512, as shown in FIG. 14.

As shown in FIG. 15, the apparatus is also suitable for use in an operating room where the surgeon does not wish to touch the exterior of the container 500 or the cap 502. In this connection, the barrier member 508 retains the swab 24 within the container 500 as the cap 502 is removed when no transverse force t is applied to the cap 502 and this in turn allows the cap 502 to be pulled free of bulbous member 528. The surgeon is then free to remove the swab 24 and the sterile bulbous member 528 from the container 500 once the cap 502 has been removed by an attendant.

As shown in the embodiment of FIGS. 10-15, the opening in the barrier member 508 is large enough to accommodate the upper portion of the absorbent tip 28 and the spacing between the barrier member 508 and the piston member 506 is sufficiently large to assure that the upper portion of the tip 28 will extend into the opening. As noted, this combination is particularly desirable when the swab is to be utilized in an aerobic combination. However, it is many times desirable to provide an anaerobic culture transport system. This may be achieved as shown in FIG. 17 by utilizing a smaller opening 524a and a greater spacing between the barrier member 508 and the piston member 506 relative to the overall axial length of the absorbent tip 28. Of course, the mere elongation of the walls 510 between the barrier member 508 and the piston member 506 will provide the increased space necessary for the anerobic application. As explained previously, a smaller hole 524a will allow a substantially air-tight seal to be formed at the stick 26.

The tape-like sealing member 504 which joins the tube or container 500 with the cap 502 in FIG. 9 may comprise a portion adapted to be written upon to allow the labeling of the transport tube. As shown in FIG. 19, this is accomplished by providing a first portion 540 carrying a suitable adhesive, preferably a pressure sensitive adhesive capable of sticking to the cap 502 and the container 500 and a second label portion 542. The adhesive portion 540 is adapted to be wrapped around the junction between the container 500 and the cap 502 with the label portion 542 flapping free so as to permit ready removal of the tape-like member 504.

Although the container 500 and the cap 502 have been shown in molded form, it will be appreciated that they may be extruded with the ends heat sealed. Where a molded cap and container are utilized, a styrene or a polypropylene have been found to be particularly suitable materials. Where an extruded cap and container are utilized, Sarlyn or a polypropylene have been found to be particularly suitable materials. Of course, the container 500 and the cap 502 may be made from a glass as well as a plastic.

As shown in FIG. 20, a bulbous portion 628 forms a seal with the hollow tubular container 500 along the surface 630 so as to eliminate the necessity for a sterile wrapping or the adhesive seal shown in FIG. 9. The area 632 above the sealing portion 630 cooperates with the cap 502 in the same manner demonstrated in FIGS. 10-14, i.e., the bulbous portion may be removed from the cap 502 as shown in those Figures.

The culture collection apparatus of FIG. 20 also comprises an integrally formed combination barrier member 608 and piston member 606 which differs somewhat from the integral combination shown in FIG. 9. As better shown in FIG. 21, the piston member comprises a valve flange 610 which is located immediately below openings 612. As the swab terminated in the absorbent tip is forced downwardly toward the bottom of the container 500 and past the barrier 608, the culture medium 20 as shown in FIG. 20 is forced between the flange 610 and the container 500. In the absence of movement of the piston 606, flange 610 forms a seal with the tubular container 500 so as to prevent the passage of air therebetween. Similarly, beads 614 which extend outwardly from the upper walls 616 of the piston member both above and below the barrier member 608 to form a seal with the container 500 so as to prevent the passage of air through the opening 612. Of course and as explained previously, this passage of air must be prevented if the apparatus is to be used with anaerobic cultures. In the alternative, the tip 28 could rest on top of the barrier 608 passing therethrough after the piston 606 comes to rest.

It will also be noted that the piston member comprises an additional flange 618 located below the flange 610 and near the bottom of the piston 606. The flange 618 along with the flange 610 forms a dead air space which traps the air before the air reaches the opening 612 thereby assuring that the apparatus may be utilized with anaerobic cultures. In some instances, the dead air space may have insufficient capacity to trap the air, and the air will then flow through the opening 612 and out the opening 624.

Additional features of the integral piston member 606 and the barrier member 608 include the tapered or conical surface 620 at the bottom of the piston member 606. The conical or tapered surface 620 assists in forcing the culture sustaining or bacteria identification medium up toward the opening 612 before bottoming out at the closed end of the container 500. In order to provide strength in the piston member, ridges 622 extend between the openings 612 from a point above the sealing bead 614 down to the flange 618. Strength is further provided within the piston member by tapering the chamber inwardly near the conical bottom surface 620.

The barrier member 608 comprises a specific configuration which assures that the opening 624 in the barrier member 608 will allow passage of the absorbent tip therethrough while at the same time forming the appropriate seal between the elongated member 26 and the edges of the opening 624. In this connection, a tangential slit 626 as best shown in FIG. 23 extends along and is tangent to the circular aperture of the opening 624. This particular combination has been found to provide the optimum in sealing engagement with the elongated member 26 while at the same time providing sufficient flexibility and elasticity for passage of the absorbent tip 28.

Details of the bulbous portion 628 are illustrated in FIG. 22. As shown therein, the sealing surface 630 comprises a pair of annular beads 632. In order to achieve the proper clearance and interaction with the cap 502, essentially longitudinally extending ribs 634 are formed along the cup-like portion 636. On the interior of the cup-like portion 636, a cylindrical portion 638 includes annular beads 640 in the central opening therein which grasp the elongated member 26. The annular space between the portion 638 and the portion 636 may be eliminated for strength.

Figure 27:
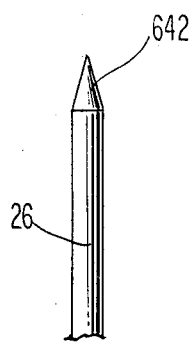
FIG. 27 is an enlarged sectional view of the end of the elongated member of the swab shown in FIG. 20.

In order to assure the proper use of the apparatus as an anaerobic culture collection apparatus, it is essential that the elongated member 26 does not provide a passageway for air to pass to the chamber in which the absorbent tip 28 is located. In this connection, it is desirable to close or heat seal the end 642 of the elongated member 26 as shown in FIGS. 20 and 27. This precludes any possibility that the elongated member 26 may serve as a conduit for the passage of air where the member 26 is otherwise hollow except for the end 642. In the alternative, the bulbous portion 628 may be terminated at one end by a hood 644 as shown in FIG. 26. These precautions are only necessary where the elongated member 26 is hollow.

As mentioned previously, the sealing surface 630, and more particularly the beads 632 of the bulbous portion 628, provide for the sterile sealing of the swab within the tube 500. It is therefore not necessary to provide a sterile wrap or the adhesive tape-like member shown in FIG. 9. However, it may be desirable to provide a tape-like member 646 as shown in FIGS. 24 and 25 for labeling. In addition, the tape-like member 646 may provide a stop so as to prevent accidental movement of the piston 606. As shown in FIGS. 24 and 25, it is very difficult to force the cap 502 downwardly over the tube 500 unless the tape-like member 646 is first removed. This assures that the culture medium 20 will not be forced upwardly into the chamber within the piston member 606 until after the swab has been utilized in collecting a culture.

Figure 28C:
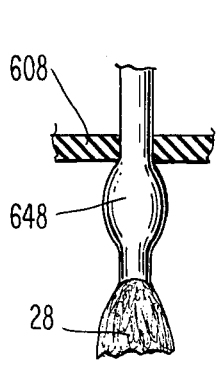
FIG. 28(a, b & c) are sectional views of alternative means for forming seals between the elongated member and the barrier member.
Figure 28B:
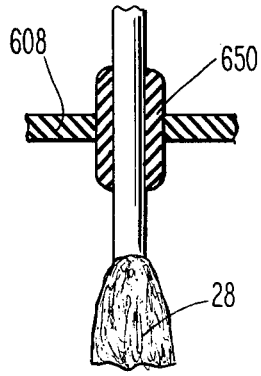
Figure 28A:
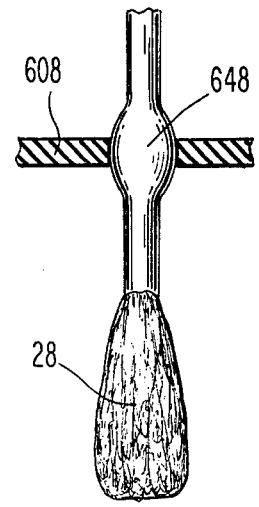

Finally, FIGS. 28a and 28b illustrate means by which the formation of a seal at the barrier member 608 may be further assured. As shown in FIG. 28a, the elongated member 26 includes an integral bulge 648. In the alternative and as shown in FIG. 28b, the enlargement or bulge provided by the portion 648 may be provided by a sleeve 650. In either case, the enlarged area is located immediately above the absorbent tip 28 so as to be lodged within the opening 624 in the barrier member 608 once the absorbent tip 28 is located within the chamber. FIG. 28c shows a variation in the embodiment of FIG. 28c wherein the portion 648 has passed through the opening in the barrier 608 and is forced upwardly by the expansive forces of the tip 28 against the bottom of the piston 606.

Figure 29:
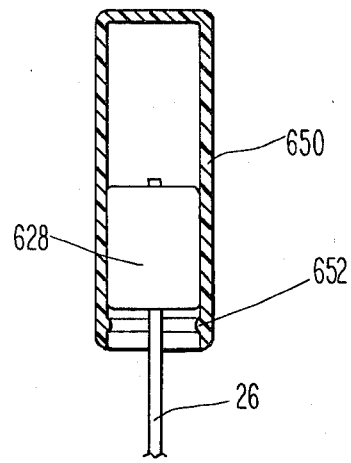
FIG. 29 is a sectional view of an alternative cap which may be used with the container of FIG. 20.

FIG. 29 shows a cap 650 which comprises an internal flange 652 adapted to form a stop for the bulbous portion 628. Note that the portion 628 is still free to move axially through said cap 650 to adjust the effective length of the elongated member 26.

Although specific embodiments of the invention have been shown and described, it will be appreciated that various modifications may be made including the incorporation of features in one embodiment into another embodiment. These modifications and others which will occur to those of ordinary skill in the art fall within the true spirit and scope of the invention as set forth in the appended claims.

I claim:

1. Apparatus for collecting cultures, said apparatus comprising:
   (a) a hollow tubular container having a closed end, an open end and sides extending therebetween;
   (b) a culture-sustaining medium position within said tubular container adjacent said closed ends;
   (c) a swab including an elongated member and an absorbent tip, said swab extending into said container; and
   (d) a movable piston means extending the cross tubular member and adapt to form a seal with said sides, said piston means being movable through said culture-sustaining medium toward said closed end when said swab is in pushing contact with said piston means, said piston means including valve means for allowing said culture-sustaining medium to flow through said valve means from a position adjacent said closed end through and into contact with said absorbent tip.

2. The apparatus of claim 1 wherein said piston means comprises a chamber receiving at least a portion of said absorbent tip.

3. The apparatus of claim 2 wherein said chamber includes an opening through which said absorbent tip may pass.

* * * * *